US012576167B2

(12) United States Patent
Chang et al.

(10) Patent No.: US 12,576,167 B2
(45) Date of Patent: Mar. 17, 2026

(54) GADOLINIUM-BASED COMPOUND, METHOD FOR PRODUCING SAME, AND MRI CONTRAST AGENT CONTAINING SAME

(71) Applicant: KYUNGPOOK NATIONAL UNIVERSITY INDUSTRY-ACADEMIC COOPERATION FOUNDATION, Busan (KR)

(72) Inventors: Yong Min Chang, Daegu (KR); Bo Kyung Sung, Daegu (KR)

(73) Assignee: KYUNGPOOK NATIONAL UNIVERSITY INDUSTRY-ACADEMIC COOPERATION FOUNDATION, Busan (KR)

( * ) Notice: Subject to any disclaimer, the term of this patent is extended or adjusted under 35 U.S.C. 154(b) by 581 days.

(21) Appl. No.: 17/794,843

(22) PCT Filed: Jan. 22, 2021

(86) PCT No.: PCT/KR2021/000883
§ 371 (c)(1),
(2) Date: Jul. 22, 2022

(87) PCT Pub. No.: WO2021/150049
PCT Pub. Date: Jul. 29, 2021

(65) Prior Publication Data

US 2023/0233714 A1 Jul. 27, 2023

(30) Foreign Application Priority Data

Jan. 22, 2020 (KR) ........................ 10-2020-0008880
Jan. 22, 2021 (KR) ........................ 10-2021-0009130

(51) Int. Cl.
*A61K 49/10* (2006.01)
*C07F 5/00* (2006.01)

(52) U.S. Cl.
CPC ............ *A61K 49/108* (2013.01); *C07F 5/003* (2013.01)

(58) Field of Classification Search
CPC .............................. A61K 49/108; C07F 5/003
See application file for complete search history.

(56) References Cited

U.S. PATENT DOCUMENTS

2002/0127629 A1 9/2002 Bogdanov et al.
2016/0251378 A1 9/2016 Schmitthenner et al.

FOREIGN PATENT DOCUMENTS

KR 20190111356 B1 10/2019

OTHER PUBLICATIONS

Endres et al., "DNA-TiO2 nanoconjugates labeled with magnetic resonance contrast C2 agents" Journal of the American Chemical Society, vol. 129, No. 51, pp. 15760-15761. (Year: 2007).*
Bogdanov et al., "Oligomerization of paramagnetic substrates result in signal amplification and can be used for MR imaging of molecular targets." Molecular imaging 2002, vol. 1, No. 1, pp. 16-23.
Endres et al., "DNA-TiO2 nanoconjugates labeled with magnetic resonance contrast agents" Journal of the american chemical society 2007, vol. 129, No. 51, pp. 15760-15761.
International Search Report and Written Opinion issued in Corresponding PCT Application No. PCT/KR2021/000883, dated Apr. 30, 2021 (English Translation provided).

* cited by examiner

*Primary Examiner* — Michael G. Hartley
*Assistant Examiner* — Jagadishwar R Samala
(74) *Attorney, Agent, or Firm* — NORTON ROSE FULBRIGHT US LLP

(57) ABSTRACT

The present invention relates to a novel gadolinium-based compound having a structure in which a gadolinium complex and a gallic acid are bonded to each other, a method for producing same, and an MRI contrast agent containing same.

12 Claims, 12 Drawing Sheets

1
2
3
4
5

GADOLINIUM-BASED COMPOUND, METHOD FOR PRODUCING SAME, AND MRI CONTRAST AGENT CONTAINING SAME

CROSS-REFERENCE TO RELATED APPLICATIONS

This application a national phase under 35 U.S.C. § 371 of International Application No. PCT/KR2021/000883 filed Jan. 22, 2021, which claims priority to KR Patent Application No. 10-2020-0008880 filed Jan. 22, 2020 and KR Patent Application No. 10-2021-0009130 filed Jan. 22, 2021. The contents of each of the referenced applications are incorporated into the present application by reference.

TECHNICAL FIELD

The present disclosure relates to a novel gadolinium-based compound, a method for preparation of the same, and an MRI contrast agent containing the same. Specifically, the present disclosure relates to a novel gadolinium-based compound having a structure in which a gadolinium complex and a gallic acid are bonded to each other via a linking group, a method for preparing the same, and an MRI contrast agent containing the same.

DESCRIPTION OF RELATED ART

Today, the number of patients with degenerative brain disease is increasing due to the aging of the population. Accordingly, the need for early detection of the disease is emerging. Degenerative brain diseases include Parkinson's disease, vascular dementia, Alzheimer's disease, and the like. Neurotoxicity due to excessive accumulation of amyloid beta polymer (oligomeric Aβ) is considered as one of the causes of the disease.

The amyloid beta (Aβ) is a major component of amyloid plaque found in a brain of an Alzheimer's patient, and refers to 36 to 43 amino acid peptides that are critically involved in the Alzheimer's disease. The peptide is derived from amyloid precursor protein (APP).

The amyloid beta molecules may aggregate with each other to form a soluble polymer that may exist in several forms. It is known that the formed amyloid beta polymer (oligomeric Aβ) is toxic to nerve cells, and excessive accumulation in the brain thereof is directly involved in the pathogenesis of Alzheimer's disease. Therefore, it was expected that sensing change in a concentration of the amyloid beta polymer would enable early diagnosis of the degenerative brain diseases.

Magnetic Resonance Image (MRI) refers to a method of obtaining anatomical, physiological, and biochemical information images of the body using a phenomenon in which the distributions of hydrogen atoms in different tissues of the body are different from each other and the hydrogen atoms are relaxed in a magnetic field. Unlike CT or PET, MRI does not use radiation harmful to the human body and creates images inside the body using the gradient of the magnetic field and radio waves under a strong magnetic field. Thus, the MRI is non-invasive, has high resolution, and has excellent soft tissue examination capabilities.

In order to use the MRI equipment more precisely, a contrast agent is injected into a subject to obtain an MRI image. The contrast between tissues on the MRI image is a phenomenon that occurs because the relaxation actions in which the nuclear spins of water molecules to return to the equilibrium state in the different tissues are different from each other. The contrast agent uses a paramagnetic or superparamagnetic material to affect the relaxation action to enhance the difference in relaxation between tissues and thus induce change in the MRI signal to make the contrast between the tissues clearer.

Currently, the most commonly used contrast agent in clinical practice is a contrast agent based on gadolinium (Gd) chelate. Currently, Gd-DTPA (Magnevist®), Gd-DOTA (Dotaram®), Gd(DTPA-BMA) (Omniscan®), Gd(DO3A-HP) (ProHance®), Gd(BOPTA) (MultiHance®), etc. are being used. However, most of the commercially available contrast agents are non-specific contrast agents distributed in the extracellular fluid (ECF). Only a liver-specific contrast agent is used as a specific contrast agent. Recent research is related to the development of a contrast agent that has a specific target or that may exhibit signal enhancement due to physiological activity (pH change, enzyme activity). Currently, sufficient results about MRI contrast agents specific to degenerative brain diseases have not been obtained.

DISCLOSURE

Technical Purpose

One purpose of the present disclosure is to provide a gadolinium-based compound that may be used as an MRI contrast material and, in particular, has specificity to degenerative brain disease.

Another purpose of the present disclosure is to provide an MRI contrast agent containing the compound.

Another purpose of the present disclosure is to provide a method for preparation of the compound.

Technical Solution

According to the present disclosure, there is provided a gadolinium-based compound represented by a following Chemical Formula 1:

(Chemical Formula 1)

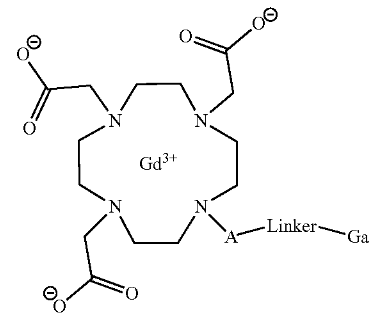

In the above Chemical Formula 1, A represents *—$(CH_2)_n$-$A^1$-*, n represents any integer from 0 to 5, $A^1$ represents *—COO—*, *—CO—*, *—NH—*, *—$CH_2$—*, *—CONH—*, or *—O—*, Linker represents *-$L^1$-NHCO-$L^2$-*, *-L-O—R—O-$L^2$-*, *-$L^1$-$CH_2$-$L^2$-*, *-L-NH-$L^2$-*, or *-$L^1$-COO-$L^2$-*, $L^1$ represents linear or branched (C1-C30)alkyl, $L^2$ represents a single bond, hydrogen or linear or branched (C1-C30)alkyl, R represents linear or branched (C1-C20)alkyl, Ga represents a following Chemical Formula 2:

(Chemical Formula 2)

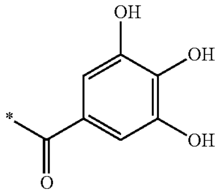

* indicates a connection site.

Further, according to the present disclosure, an MRI contrast agent containing the gadolinium-based compound represented by the Chemical Formula 1 is provided.

Further, according to one embodiment of the present disclosure, there is provided a method for preparing the gadolinium-based compound represented by the Chemical Formula 1, the method comprising following steps:

(a) reacting a compound represented by a following Chemical Formula 1-1 with a halogen compound to obtain a following Chemical Formula 1-2:

(Chemical Formula 1-1)

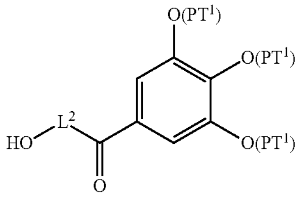

(Chemical Formula 1-2)

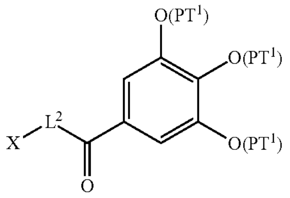

wherein in each of the Chemical Formulas 1-1 and 1-2, $PT^1$ represents a protecting group, X represents a halogen atom, $L^2$ is the same as previously defined in the Chemical Formula 1;

(b) reacting the compound of the Chemical Formula 1-2 with a compound represented by a following Chemical Formula 1-3 to obtain a compound represented by a following Chemical Formula 1-4, (Chemical Formula 1-3)

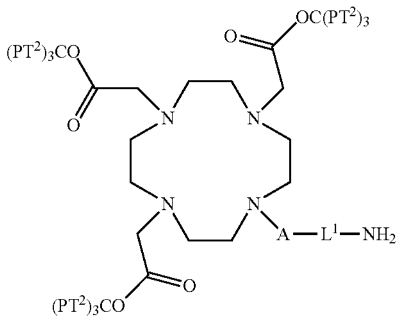

-continued (Chemical Formula 1-4)

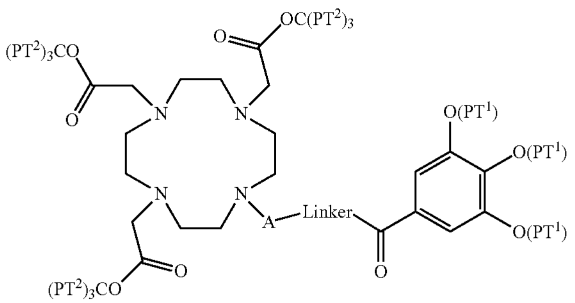

wherein in each of the Chemical Formulas 1-3 and 1-4, each of $PT^1$ and $PT^2$ individually represents a protecting group, Linker represents *-$L^1$-NH-$L^2$-*, each of $L^1$, $L^2$, and A is as previously defined in the Chemical Formula 1;

(c) removing $PT^1$ and $PT^2$ from the compound of the Chemical Formula 1-4; and (d) reacting a compound obtained in the step (c) with gadolinium hydrate to obtain the compound of the Chemical Formula 1.

Further, according to another embodiment of the present disclosure, there is provided a method for preparing the gadolinium-based compound represented by the Chemical Formula 1, the method comprising following steps:

(a) reacting a compound represented by a following Chemical Formula 2-1 with a compound represented by a following Chemical Formula 2-2 to obtain a following Chemical Formula 2-3:

(Chemical Formula 2-1)

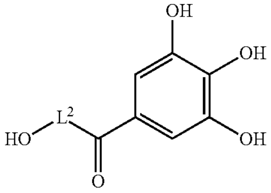

(Chemical Formula 2-2)

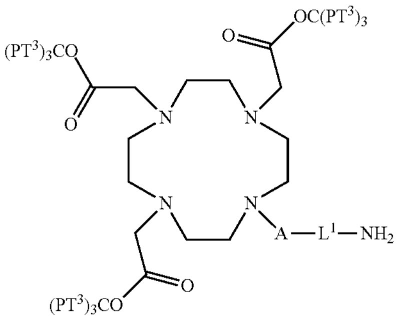

-continued (Chemical Formula 2-3)

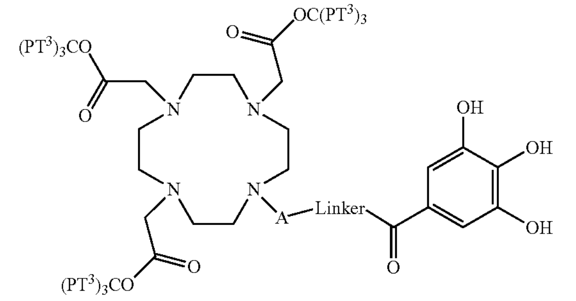

wherein in each of the Chemical Formulas 2-1 to 2-3, $PT^3$ represents a protecting group, Linker represents *-$L^1$-NH-$L^2$-*, each of $L^1$, $L^2$, and A is the same as previously defined in the Chemical Formula 1;

(b) removing $PT^3$ from the compound of the Chemical Formula 2-3; and (c) reacting a compound obtained in the step (b) with gadolinium hydrate to obtain the compound of the Chemical Formula 1.

Technical Effects

The novel gadolinium-based compound according to the present disclosure not only has sufficient self-relaxation properties to be used as an MRI contrast material, but also binds to amyloid beta polymer (oligomeric Aβ), so that the compound has an MRI contrast enhancing effect in the presence of the amyloid beta polymer (oligomeric Aβ), and thus may be used for diagnosis of diseases related to the amyloid beta polymer (oligomeric Aβ), specifically, the degenerative brain disease.

DETAILED DESCRIPTIONS

Figure 1A:
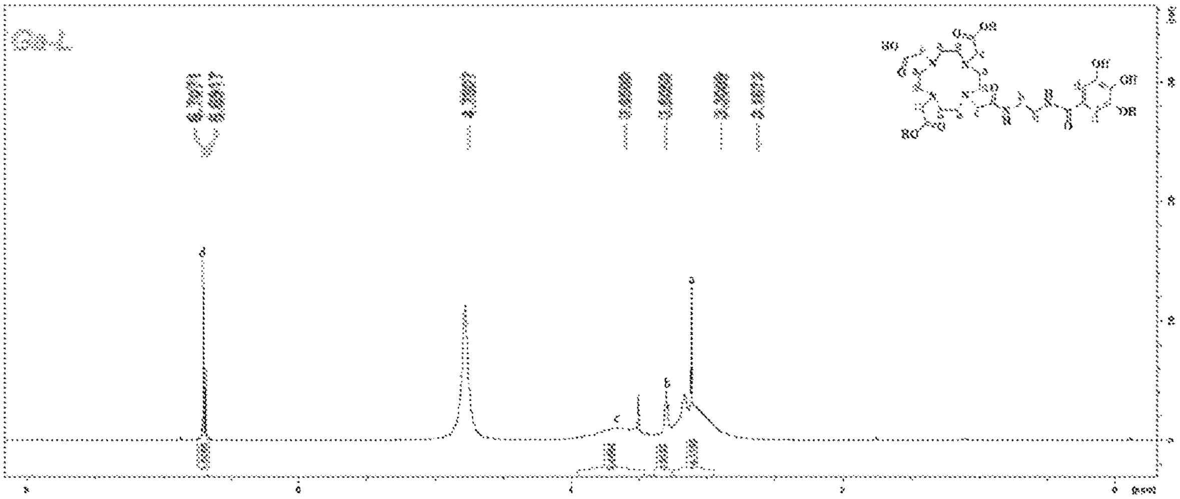
FIG. 1A is a $^1$H NMR spectrum of a compound 6 prepared in Present Example 1 of a compound according to the present disclosure.

The terminology used herein is for the purpose of describing particular embodiments only and is not intended to be limiting of the present disclosure. Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A gadolinium-based compound according to the present disclosure may be represented by a following Chemical Formula 1:

(Chemical Formula 1)

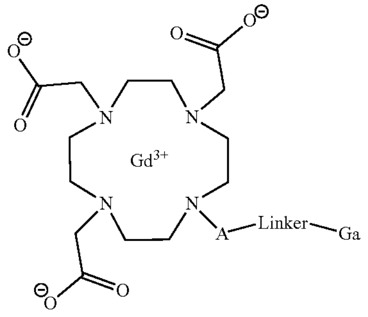

In the above Chemical Formula 1, A represents *—$(CH_2)_n$-$A^1$-*, n may represent any integer from 0 to 5, specifically any integer from 1 to 5, and more specifically, any integer from 1 to 3, $A^1$ represents *—COO—*, *—CO—*, *—NH—*, *—$CH_2$—*, *—CONH—*, or *—O—*, Linker represents *-$L^1$-NHCO-$L^2$-*, *-$L^1$-O—R—O-$L^2$-*, *-$L^1$-$CH_2$-$L^2$-*, *-$L^1$-NH-$L^2$-*, or *-$L^1$-COO-$L^2$-*, specifically, *-$L^1$-$CH_2$-$L^2$-*, $L^1$ represents linear or branched (C1-C30)alkyl, specifically, linear or branched (C1-C10)alkyl, more specifically, linear or branched (C1-C5)alkyl, $L^2$ represents a single bond, hydrogen or linear or branched (C1-C30)alkyl, specifically, a singe bond, R represents linear or branched (C1-C20)alkyl, specifically, linear or branched (C1-C10)alkyl, more specifically, linear or branched (C1-C5)alkyl, Ga represents a following Chemical Formula 2:

(Chemical Formula 2)

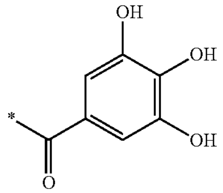

* indicates a connection site.

According to one embodiment of the present disclosure, in the Chemical Formula 1, n may represent any integer from 1 to 5, and $A^1$ may represent *—CONH—*.

According to another embodiment of the present disclosure, $L^1$ may represent linear or branched (C1-C10)alkyl, and $L^2$ may represent the single bond.

In the gadolinium-based compound of the Chemical Formula 1, gadolinium may be coordinated with at least one water molecule. For example, in the gadolinium-based compound of the Chemical Formula 1, gadolinium may coordinate with one or two water molecules.

In the gadolinium-based compound of the Chemical Formula 1 of the present disclosure, when $A^1$ is *—COO—*, *—CO—*, or *—CONH—*, an oxygen atom may form a coordination bond with gadolinium.

The Chemical Formula 2 of the present disclosure is a portion derived from a gallic acid. The gallic acid is a polyphenol compound as a chemical substance found in plants, and contains two or more phenol groups in one molecule thereof, and has been used as a major component of anti-aging agents and disease-treatment agents for diseases because of its antioxidant effect. The use of the gallic acid for an MRI contrast agent with a targeting function toward amyloid beta polymer (oligomeric Aβ) has not been considered until now.

The gadolinium-based compound of the Chemical Formula 1 of the present disclosure may specifically bind to mammalian amyloid beta polymer (oligomeric Aβ), as shown in Examples to be described later.

Further, the compound according to the present disclosure is water-soluble and coordinates with at least one or more water molecules and thus has magnetic-relaxation properties. Thus, the compound increases the relaxation of at least one or more water molecules and hydrogen atoms in the human body to improve the image contrast, and thus may be used as an MRI contrast material.

Accordingly, according to the present disclosure, an MRI contrast agent containing a gadolinium-based compound represented by the Chemical Formula 1 is provided. Further, since the compound according to the present disclosure is capable of binding to the amyloid beta polymer (oligomeric Aβ), the MRI contrast agent according to the present disclosure may be used to diagnose a disease associated with amyloid beta polymer (oligomeric Aβ), more specifically, degenerative brain diseases such as Parkinson's disease, vascular dementia, Alzheimer's disease. Accordingly, according to one embodiment of the present disclosure, a specific MRI contrast agent for diagnosing degenerative brain disease containing the compound of the Chemical Formula 1 may be provided. Moreover, as described above, according to a recent study, the amyloid beta polymer (oligomeric Aβ) induced by amyloid precursor protein is excessively accumulated in the brain and thus was involved in onset of Alzheimer's disease. Therefore, an MRI contrast agent containing the compound according to the present disclosure targeting the amyloid beta polymer (oligomeric Aβ) may act as a specific MRI contrast agent for the diagnosis of Alzheimer's disease, especially for early diagnosis thereof.

Further, according to one embodiment of the present disclosure, there is provided a method for preparing the gadolinium-based compound represented by the Chemical Formula 1, the method comprising following steps:

(a) reacting a compound represented by a following Chemical Formula 1-1 with a halogen compound to obtain a following Chemical Formula 1-2:

(Chemical Formula 1-1)

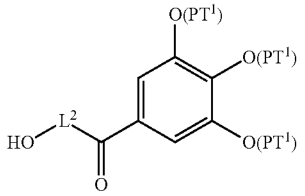

(Chemical Formula 1-2)

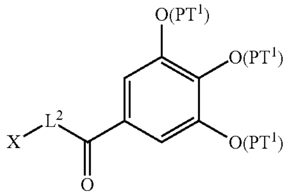

wherein in each of the Chemical Formulas 1-1 and 1-2, $PT^1$ represents a protecting group, X represents a halogen atom, $L^2$ is the same as previously defined in the Chemical Formula 1;

(b) reacting the compound of the Chemical Formula 1-2 with a compound represented by a following Chemical Formula 1-3 to obtain a compound represented by a following Chemical Formula 1-4, (Chemical Formula 1-3)

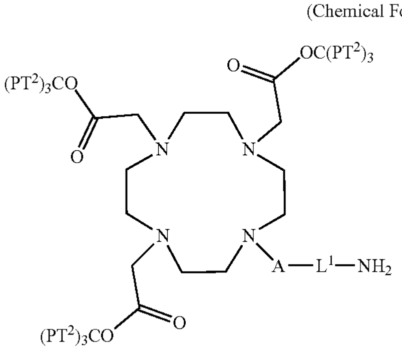

-continued (Chemical Formula 1-4)

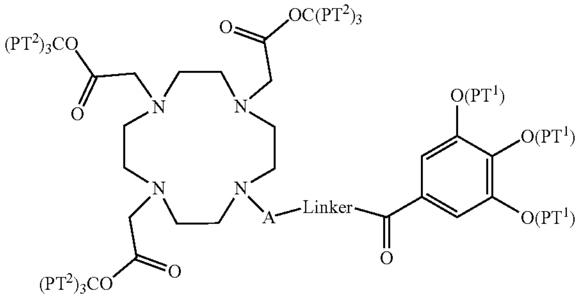

wherein in each of the Chemical Formulas 1-3 and 1-4, each of $PT^1$ and $PT^2$ individually represents a protecting group, Linker represents *-$L^1$-NH-$L^2$-*, each of $L^1$, $L^2$, and A is as previously defined in the Chemical Formula 1;

(c) removing $PT^1$ and $PT^2$ from the compound of the Chemical Formula 1-4; and (d) reacting a compound obtained in the step (c) with gadolinium hydrate to obtain the compound of the Chemical Formula 1.

According to one embodiment of the present disclosure, in the step (a), $L^2$ may be a single bond, and the halogen compound may be thionyl chloride.

In the above Chemical formulas 1-1, 1-2, and 1-4, $PT^1$ may represent a protecting group which may include a protecting group commonly used for protecting a —OH group, for example, acetyl, benzoyl, methoxymethyl ether, methylthiomethyl ether or the like.

In the above Chemical Formulas 1-3 and 1-4, $PT^2$ may represent a protecting group, which may include a protecting group commonly used for protecting a —COOH group, for example, methyl, benzyl, tert-butyl, or the like.

The step (c) refers to a step for removing the protecting group, where the protecting groups, that is, $PT_1$ and $PT_2$ may be removed using a method commonly used in the art, for example, using an aqueous base or an aqueous acid.

Further, according to another embodiment of the present disclosure, there is provided a method for preparing the gadolinium-based compound represented by the Chemical Formula 1, the method comprising following steps:

(a) reacting a compound represented by a following Chemical Formula 2-1 with a compound represented by a following Chemical Formula 2-2 to obtain a following Chemical Formula 2-3:

(Chemical Formula 2-1)

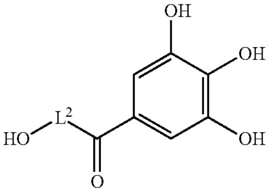

-continued (Chemical Formula 2-2)

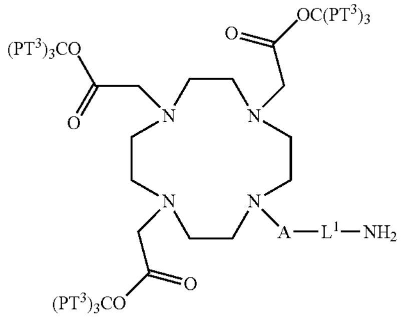

(Chemical Formula 2-3)

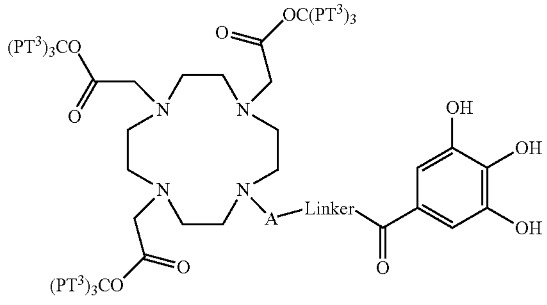

wherein in each of the Chemical Formulas 2-1 to 2-3, $PT^3$ represents a protecting group, Linker represents *-$L^1$-NH-$L^2$-*, each of $L^1$, $L^2$, and A is the same as previously defined in the Chemical Formula 1;

(b) removing $PT^3$ from the compound of the Chemical Formula 2-3; and (c) reacting a compound obtained in the step (b) with gadolinium hydrate to obtain the compound of the Chemical Formula 1.

According to one embodiment of the present disclosure, in the step (a), $L^2$ may be a single bond. That is, the compound of the Chemical Formula 2-1 may be gallic acid.

In the above Chemical Formulas 2-2 and 2-3, $PT^3$ may represent a protecting group, which may include a protecting group commonly used for protecting a —COOH group, for example, methyl, benzyl, tert-butyl, or the like.

The step (b) refers to a step for removing the protecting group, where the protecting group, that is, $PT^3$ may be removed using a method commonly used in the art, for example, using an aqueous base or an aqueous acid.

Hereinafter, for a detailed understanding of the present disclosure, the compound according to the present disclosure, the method for preparing the same, and characteristics of the MRI contrast agent containing the same will be described based on a representative compound according to the present disclosure.

Figure 8:
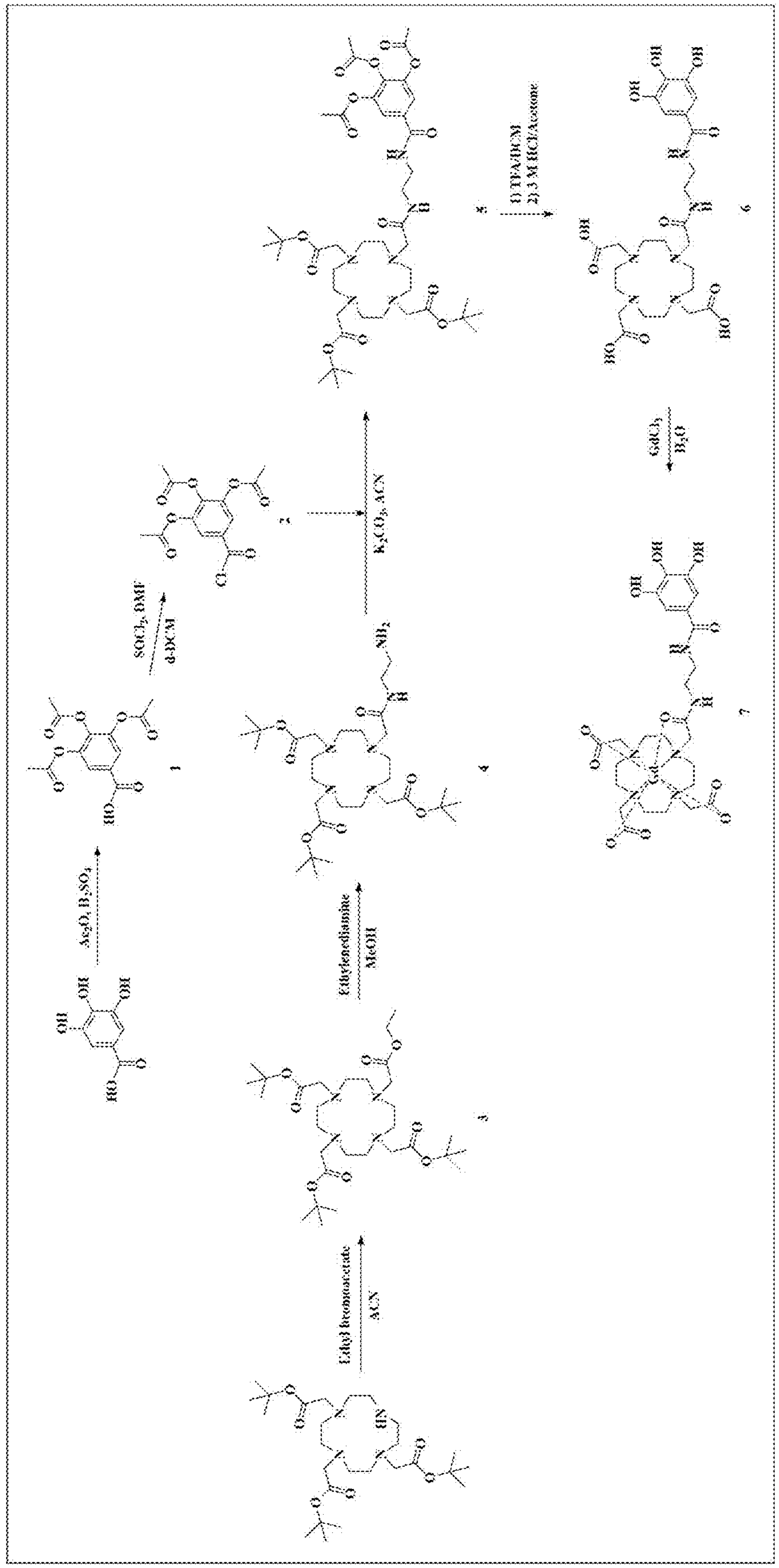
FIG. 8 shows preparation of 3,4,5-triacetoxybenzoic acid.

1. Preparation Example of Compound According to the Present Disclosure (Present Example 1, referring to FIG. 8)

1) Preparation of 3,4,5-triacetoxybenzoic acid (Compound 1)

Acetic anhydride (11.34 mL, 120 mmol) was added to gallic acid (3.76 g, 20 mmol) to produce a mixed solution. A small amount of 95% concentrated sulfuric acid was added thereto and the mixed solution was stirred for 1 hour until the solution became completely clear. Then, distilled water (100 mL) was added thereto and the mixed solution was stirred for 2.5 hours to remove residual acetic anhydride therefrom. A resulting product was filtered to obtain a solid, and then the solid was washed with distilled water (3×100 mL) and dried to obtain a white solid material (Compound 1). (Yield: 5.92 g (100%))

2) Synthesis of 5-(chlorocarbonyl)benzene-1,2,3-triyl triacetate (Compound 2)

Thionyl chloride (1.76 mL, 20 mmol) was dissolved in dimethylformamide (DMF) (200 l) to produce a mixed solution. Then, the mixed solution was slowly added to a further mixed solution in which the compound 1 (2.96 g, 10 mmol) was dissolved in dichloromethane (25 mL). A resulting mixture was stirred at 60° C. for 6 hours, and the solvent was removed therefrom via filtration under reduced pressure, and toluene was added thereto, and then, filtration under reduced pressure was repeated three times thereon to obtain a white solid (Compound 2). No further purification was carried out.

3) Synthesis of tri-tert-butyl 2,2',2"-(10-(2-ethoxy-2-oxoethyl)-1,4,5,10-tetraazacyclododecane-1,4,7-triyl)triacetate (Compound 3)

Tri-tert-butyl 2,2',2"-(1,4,7,10-tetraazacyclododecane-1,4,7-triyl)triacetate (5 g, 9.72 mmol) was dissolved in acetonitrile (160 mL) to produce a mixed solution. Then, potassium hydrogen carbonate (2.96 g, 29.69 mmol) was added thereto and the mixed solution was stirred for 30 mins. Then, ethyl bromoacetate (1.18 mL, 10.69 mmol) was added thereto and the mixed solution was stirred at 60° C. for 24 hours. After the stirring, a resulting product was filtered through a filter, and the solvent was removed therefrom via filtration under reduced pressure. A resulting product was dissolved in dichloromethane, and then, undissolved substances were removed therefrom, and all solvents were removed therefrom, and a resulting product was vacuum-dried to obtain a yellow solid material (Compound 3). (Yield: 5.8 g (99%))

4) Synthesis of tri-tert-butyl 2,2',2"-(10-(2-((2-aminoethyl)amino)-2-oxoethyl)-1,4,7,10-tetraazacyclododecane-1,4,7-triyl)triacetate (Compound 4)

The obtained compound 3 (3.2 g, 5.33 mmol) was dissolved in methanol (7 mL) to produce a mixed solution and ethylenediamine (6 mL) was added thereto, followed by reaction at room temperature for 4 days. Thereafter, the solvent was removed therefrom by heating the solution to 55° C. under vacuum to obtain an oily solid, which in turn was washed several times with ethyl ether. The washed solid was subjected to vacuum drying, and substances insoluble in methanol were removed therefrom via filtration. Then, open column chromatography thereon was performed under a dichloromethane/methanol condition to separate and purify a yellow solid (Compound 4). (Yield: 1.87 g (57%))

5) Synthesis of tri-tert-butyl 2,2',2"-(10-(2-oxo-2-((2-(3,4,5-triacetoxybenzamido)ethyl)amino)ethyl)-1,4,7,10-tetraazacyclododecane-1,4,7-triyl)triacetate (Compound 5)

The compound 4 (0.4 g, 1.27 mmol) was dissolved in acetonitrile to produce a mixed solution, and then, potassium carbonate (0.053 g, 3.81 mmol) was added thereto and reaction occurred for 30 minutes, and then the compound 2 was added thereto and the mixed solution was stirred at room temperature for 20 hours. Thereafter, a solid was removed therefrom with a filter, and the solvent was removed therefrom via filtration under reduced pressure, and then, a resulting product was subjected to separation and purification using high performance liquid chromatography under a distilled water/acetonitrile to which 0.1% trifluoroacetic acid was added. Thus, a yellow solid substance (Compound 5) was obtained.

6) Synthesis of 2,2',2"-(10-(2-oxo-2((2-(3,4,5-trihydroxybenzamido)ethyl)amino)ethyl)-1,4,7,10-tetraazacyclododecane-1,4,7-triyl)triacetic acid (Compound 6)

Figure 1B:
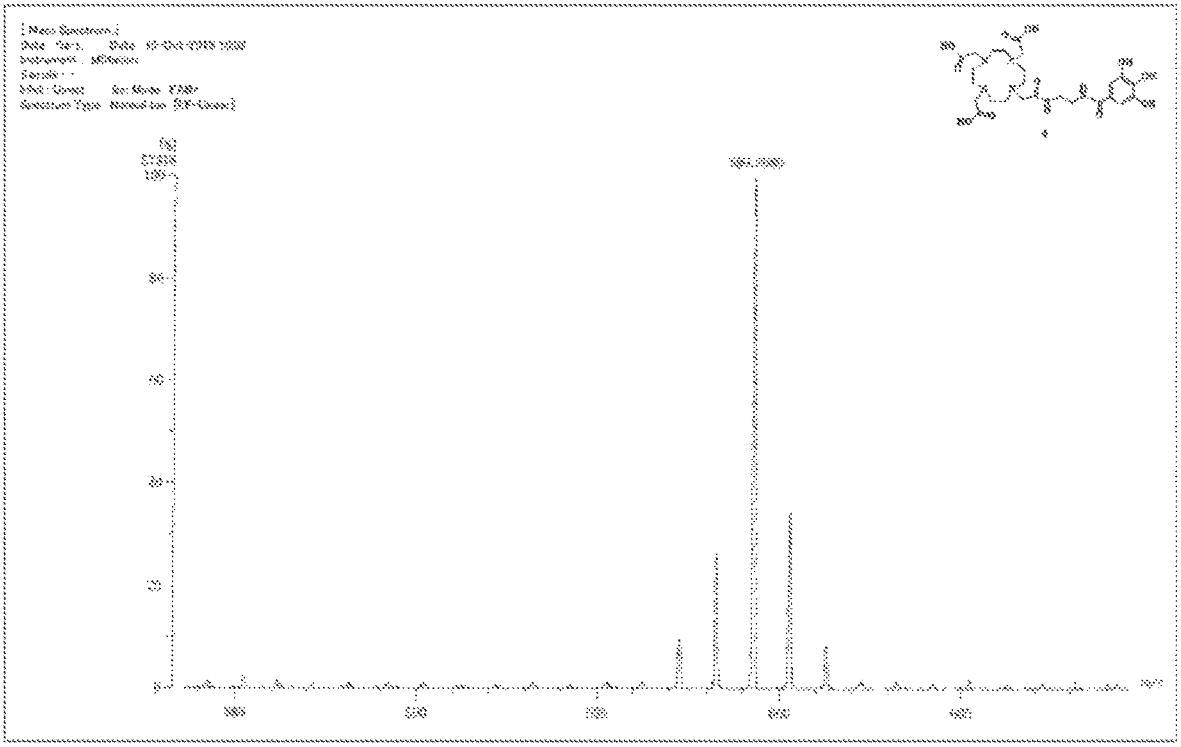
FIG. 1B is a HR-ESI-MS spectrum of the compound 6 prepared in Present Example 1 of a compound according to the present disclosure.

Trifluoroacetic acid (2 mL) was added to the Compound 5 (0.65 g, 0.73 mmol) at −4° C. to produce a mixed solution, and then the mixed solution was stirred for 20 hours, and then dichloromethane was added thereto. Then, the mixed solution was subjected to filtration under reduced pressure three times. A resulting product was dissolved in acetone (45 mL), and 3M HCl (10.5 mL) was added thereto, and the mixed solution was heated at 70° C. and stirred for 6 hours. Then, a resulting product was subjected to separation and purification using high performance liquid chromatography under a distilled water/acetonitrile to which 0.1% trifluoroacetic acid was added. Thus, a brown solid substance (Compound 6) was obtained. (Yield: 0.25 g (71%)). $^1$H NMR spectrum and HR-ESI-MS spectrum of the obtained Compound 6 are shown in FIG. 1A and FIG. 1B, respectively.

$^1$H NMR (Methanol-$d_4$); δ=2.96-3.25 (m, 16H, $CH_2$ in the cyclen ring), 3.25-3.39 (m, 4H, $CH_2$), 3.47-3.95 (m, 8H, $CH_2$), 6.67-6.73 (m, 2H, ArH)

HR-ESI-MS (m z): $[M+H]^+$ calculated for $C_{25}H_{39}N_6O_{11}$, 599.2677; found, 599.2680

7) Synthesis of Compound Gd-DO3A-Ga (Compound According to the Present Disclosure)

Figure 2A:
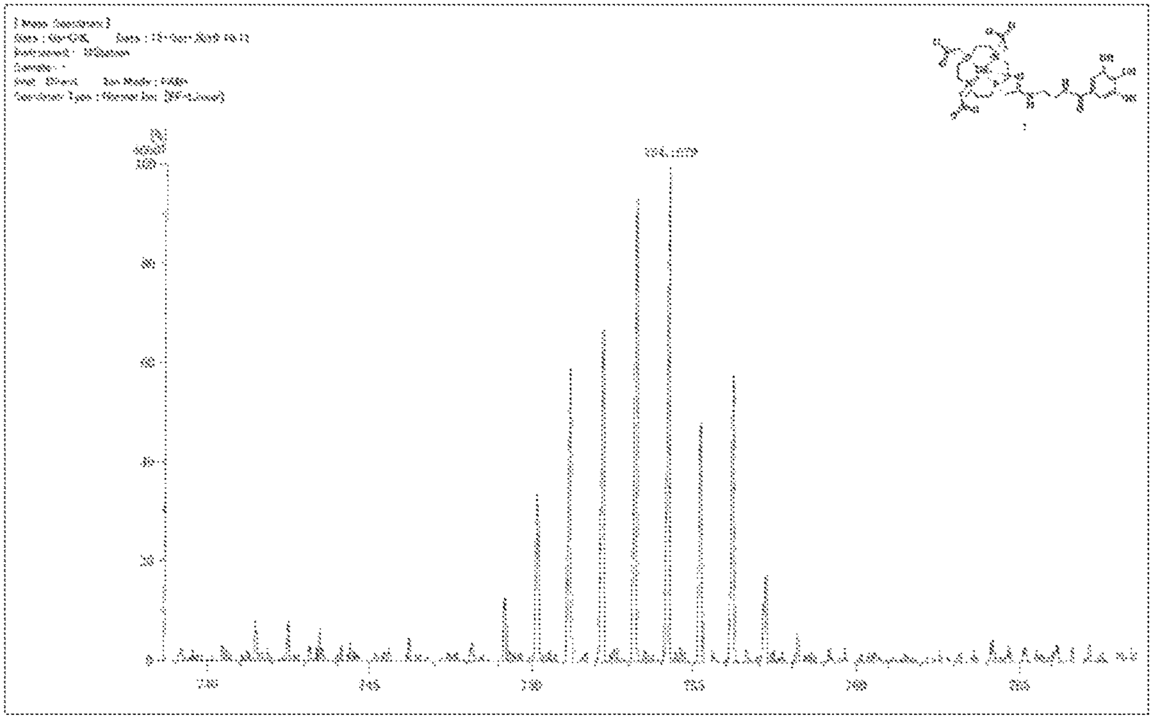
FIG. 2A is a HR-ESI-MS spectrum of Gd-DO3A-Ga prepared in Present Example 1 of a compound according to the present disclosure.
Figure 2B:
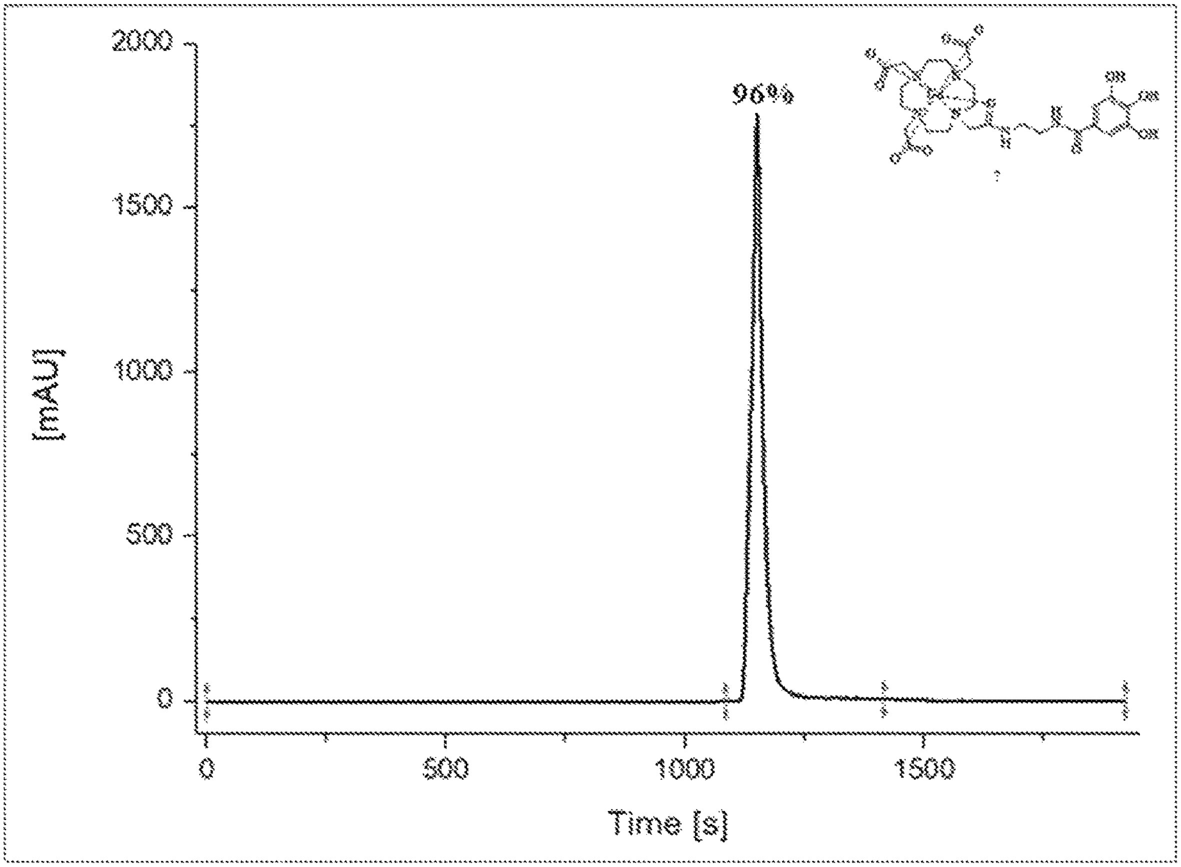
FIG. 2B is an HPLC chromatogram of Gd-DO3A-Ga prepared in Present Example 1 of a compound according to the present disclosure.

The Compound 6 (0.31 g, 0.518 mmol) was dissolved in distilled water to produce a mixed solution. pH thereof was adjusted to pH 3 using 1M sodium hydroxide. A further mixed solution in which $Gd(Cl)_3{\cdot}6H_2O$ (0.17 g, 0.47 mmol) dissolved in distilled water (500 μl) was added thereto. pH thereof was adjusted to 7 using 1M sodium hydroxide, and the mixed solution was stirred at room temperature for 20 hours. After completion of the stirring, a resulting product was subjected to filtration under reduced pressure to obtain a solid. The solid was subjected to separation and purification using high performance liquid chromatography under a distilled water/acetonitrile. Thus, a brown solid substance (compound Gd-DO3A-Ga) was obtained. HR-ESI-MS spectrum and HPLC chromatogram of the obtained compound Gd-DO3A-Ga are shown in FIG. 2A and FIG. 2B, respectively. (Yield: 0.13 g (33%)).

HR-ESI-MS (m/z): $[M+H]^+$ calculated for $C_{25}H_{35}GdN_6O_{11}$, 754.1683; found, 754.1679, Purity analysis using analytical HPLC: 96%

Figure 9:
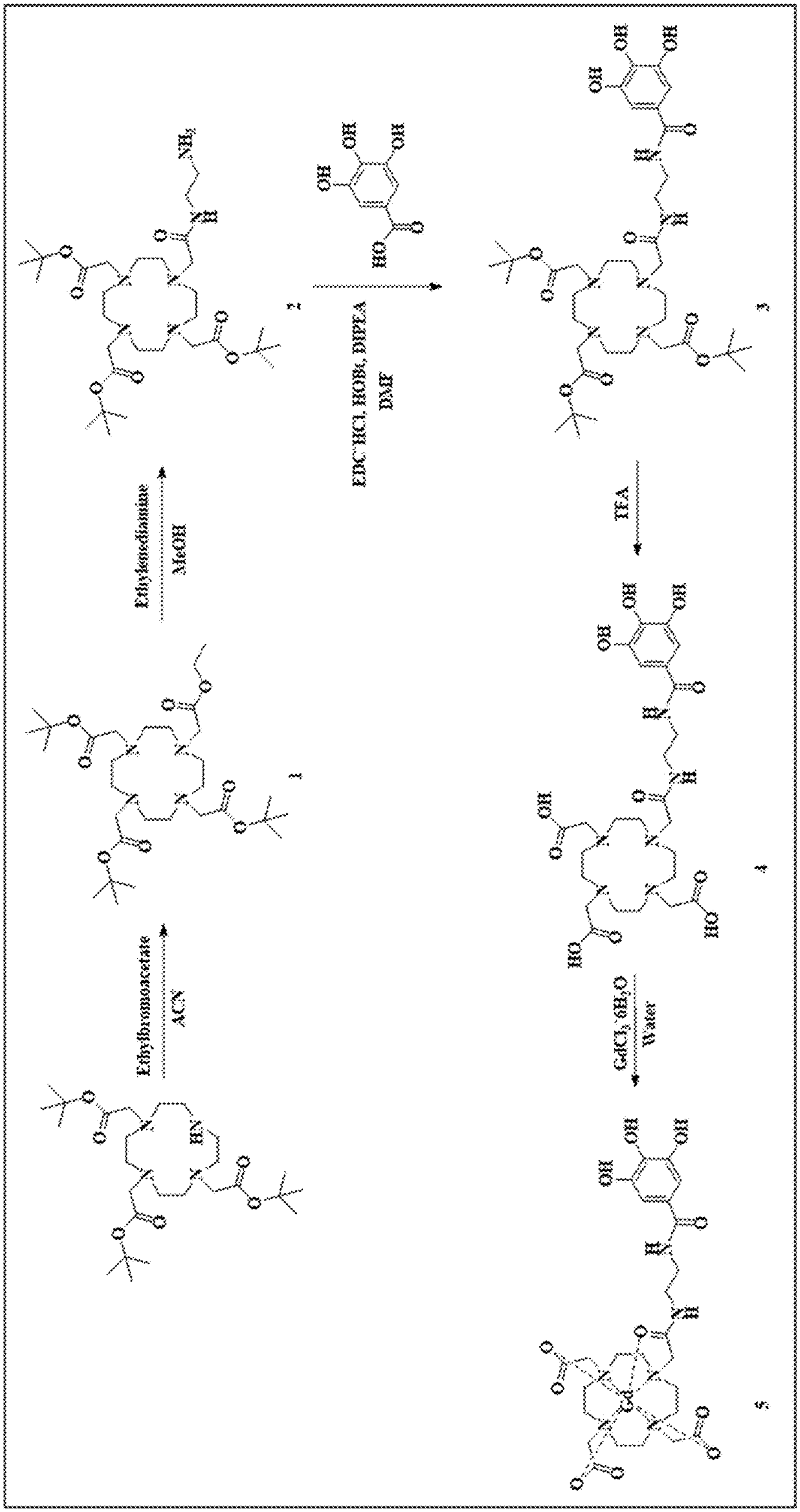
FIG. 9 shows synthesis of tri-tert-butyl 2,2', 2"-(10-(2-ethoxy-2-oxoethyl)-1,4,5,10-tetraazacyclododecane-1,4,7-triyl)triacetate.

Present Example 2, referring to FIG. 9)

1) Synthesis of tri-tert-butyl 2,2',2"-(10-(2-ethoxy-2-oxoethyl)-1,4,5,10-tetraazacyclododecane-1,4,7-triyl)triacetate (Compound 1)

Tri-tert-butyl 2,2',2"-(1,4,7,10-tetraazacyclododecane-1,4,7-triyl)tri acetate (5 g, 9.72 mmol) was dissolved in 160 mL of acetonitrile to produce a mixed solution, and then potassium hydrogen carbonate (2.96 g, 29.69 mmol) was added thereto and the mixed solution was stirred for 30 mins. Then, ethyl bromoacetate (1.18 mL, 10.69 mmol) was added thereto and the mixed solution was stirred at 60° C. for 24 hours. After the 24 hours, a resulting product was filtered through a filter, and the solvent was removed therefrom via filtration under reduced pressure. A resulting product was dissolved in dichloromethane, and undissolved substances were removed therefrom, and all solvents were removed therefrom, and then a resulting product was vacuum-dried to obtain a yellow solid material (Compound 1). (Yield. 5.8 g (99%))

2) Synthesis of tri-tert-butyl 2,2',2"-(10-(2-((2-aminoethyl)amino)-2-oxoethyl)-1,4,7,10-tetraazacyclododecane-1,4,7-triyl)tri acetate (Compound 2)

The obtained compound 1 (3.2 g, 5.33 mmol) was dissolved in methanol (7 mL) to produce a mixed solution, and then ethylenediamine (6 mL) was added thereto, followed by reaction at room temperature for 4 days. Thereafter, the solvent was removed therefrom by heating the solution to 55° C. under vacuum to obtain an oily solid, which in turn was washed several times with ethyl ether. The washed solid was subjected to vacuum drying, and substances insoluble in methanol were removed therefrom via filtration. Then, open column chromatography thereon was performed under a dichloromethane/methanol condition to separate and purify a yellow solid (Compound 2). (Yield: 1.87 g (57%))

3) Synthesis of tri-tert-butyl 2,2',2"-(10-(2-oxo-2-((2-(3,4,5-triacetoxybenzamido)ethyl)amino)ethyl)-1,4,7,10-tetraazacyclododecane-1,4,7-triyl)triacetate (Compound 3)

Gallic acid (2.18 g, 11.61 mmol) was dissolved in dimethylformamide to produce a mixed solution and then the mixed solution was stirred at 0° C. Then, a further solution in which EDC (2.45 g, 12.77 mmol) and hydroxybenzotriazole (HOBt hydrate) (1.75 g, 12.77 mmol) were dissolved in dimethylformamide were added to the gallic acid solution as the mixed solution, and then, the mixed solution was stirred for 30 minutes. Then, a further solution in which the Compound 2 (5 g, 8.13 mmol) was dissolved in dimethylformamide was added to the mixed solution. Then, DIPEA (4.04 mL, 23.22 mmol) was added thereto, followed by stirring at room temperature for 24 hours. Next, dimethylformamide was concentrated as much as possible via filtration under reduced pressure. Then, a resulting product was subjected to extraction using dichloromethane and brine, and was dehydrated with sodium sulfate, and was filtered under reduced pressure. Thereafter, open column chromatography was performed thereon under a dichloromethane/methanol condition to separate and purify a solid (Compound 3). A subsequent reaction thereof was performed without further separation and purification.

4) Synthesis of 2,2',2"-(10-(2-oxo-2((2-(3,4,5-trihydroxybenzamido)ethyl)amino)ethyl)-1,4,7,10-tetraazacyclododecane-1,4,7-triyl)triacetic acid (Compound 4)

Trifluoroacetic acid was added, in an excessive amount, to the Compound 3 at 0° C. to produce a mixture and then the mixture was stirred at room temperature for 20 hours. Thereafter, dichloromethane was added thereto, and filtration under reduced pressure was repeated thereon. A resulting product was subjected to high-performance liquid chromatography under water/acetonitrile to which 0.1% trifluoroacetic acid was added, thereby obtaining a purified solid (Compound 4). Yield (2→4): 2.1 g (43%)

Figure 3A:
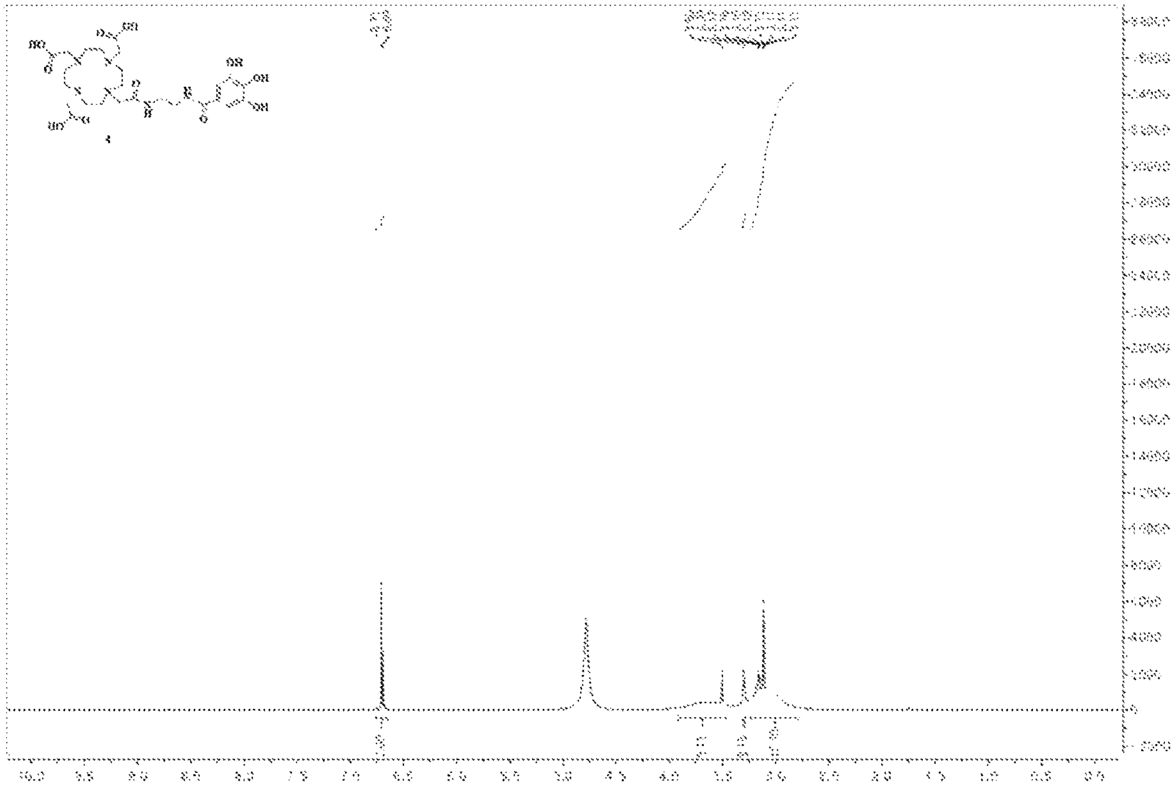
FIG. 3A is a $^1$H NMR spectrum of a compound 4 prepared in Present Example 2 of a compound according to the present disclosure.
Figure 3B:
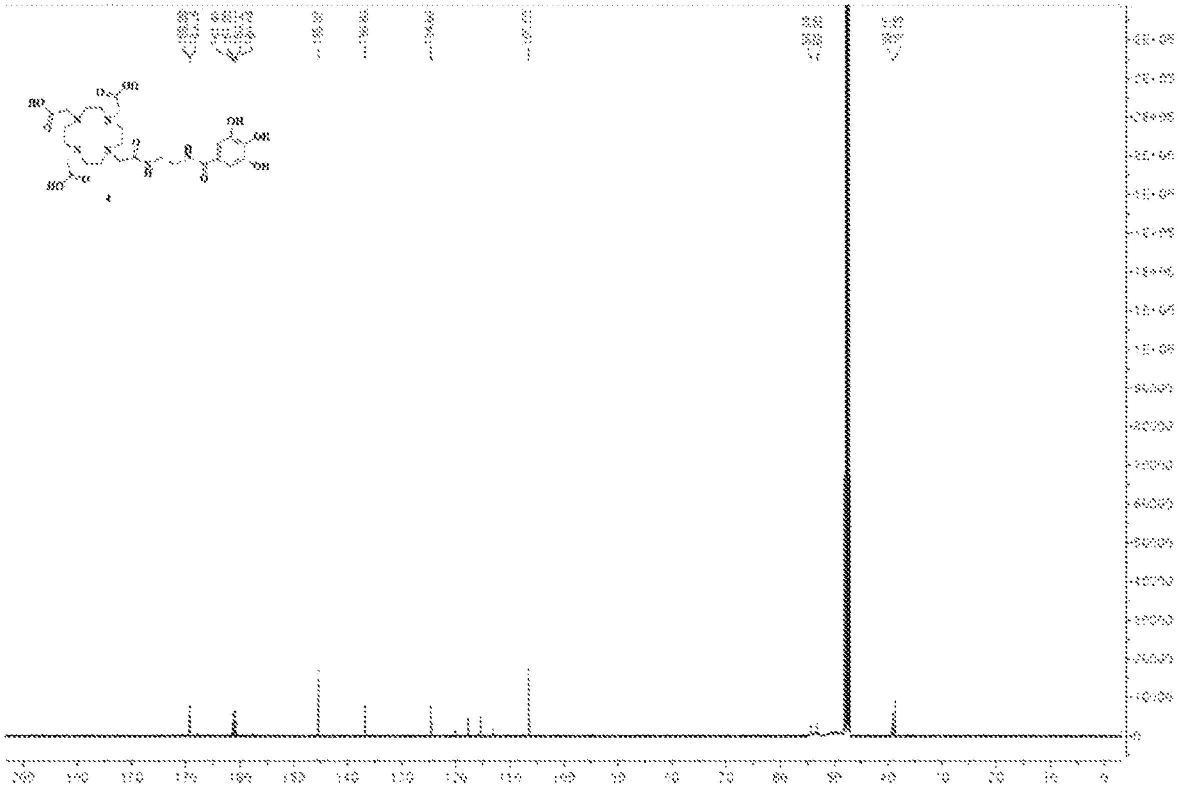
FIG. 3B is a $^{13}$C NMR spectrum of a compound 4 prepared in Present Example 2 of a compound according to the present disclosure.
Figure 3C:
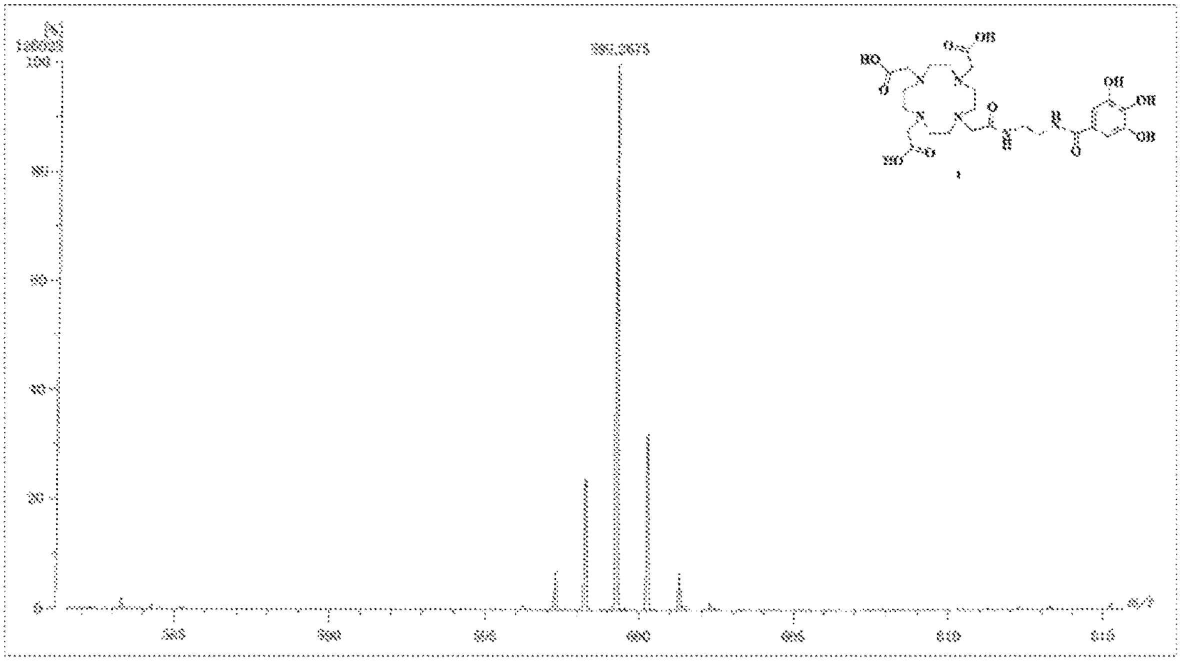
FIG. 3C is an HR-MS spectrum of the compound 4 prepared in Present Example 2 of a compound according to the present disclosure.

$^{1}H$ NMR spectrum, $^{13}C$ NMR spectrum and HR-MS spectrum of the obtained Compound 4 are shown in FIG. 3A to FIG. 3C, respectively.

$^{1}H$ NMR (500 MHz, MeOD); δ=6.70 (d, J=7.7 Hz, 2H), 3.91-3.46 (m, 8H), 3.31-3.28 (m, 2H), 3.24-2.78 (m, 18H).

$^{13}C$ NMR (126 MHz, MeOD); δ=169.29, 169.26, 161.48, 161.20, 160.92, 160.64, 145.37, 136.80, 124.60, 106.60, 54.34, 53.20, 39.15, 38.75.

HR-MS (m/z): $[M+H]^+$ calculated for $C_{25}H_{39}N_6O_{11}$, 599.2677; found, 599.2680.

5) Synthesis of Compound Gd-DO3A-Ga (Compound According to the Present Disclosure)

The Compound 4 (1 g, 1.67 mmol) was dissolved in distilled water to produce a mixed solution and then, pH thereof was adjusted to pH 3 using 1 M sodium hydroxide, and then a further mixed solution in which $Gd(Cl)_3 \cdot 6H_2O$ (0.43 g, 1.17 mmol) was dissolved in distilled water was added thereto. pH thereof was adjusted to pH 7 using 1 M sodium hydroxide, and the mixed solution was stirred at room temperature for 20 hours. After completion of the stirring, a resulting product was subjected to filtration under reduced pressure to obtain a solid. The solid was subjected to separation and purification using high performance liquid chromatography under a distilled water/acetonitrile. Thus, a solid material (Compound Gd-DO3A-Ga) was obtained.

Figure 4A:
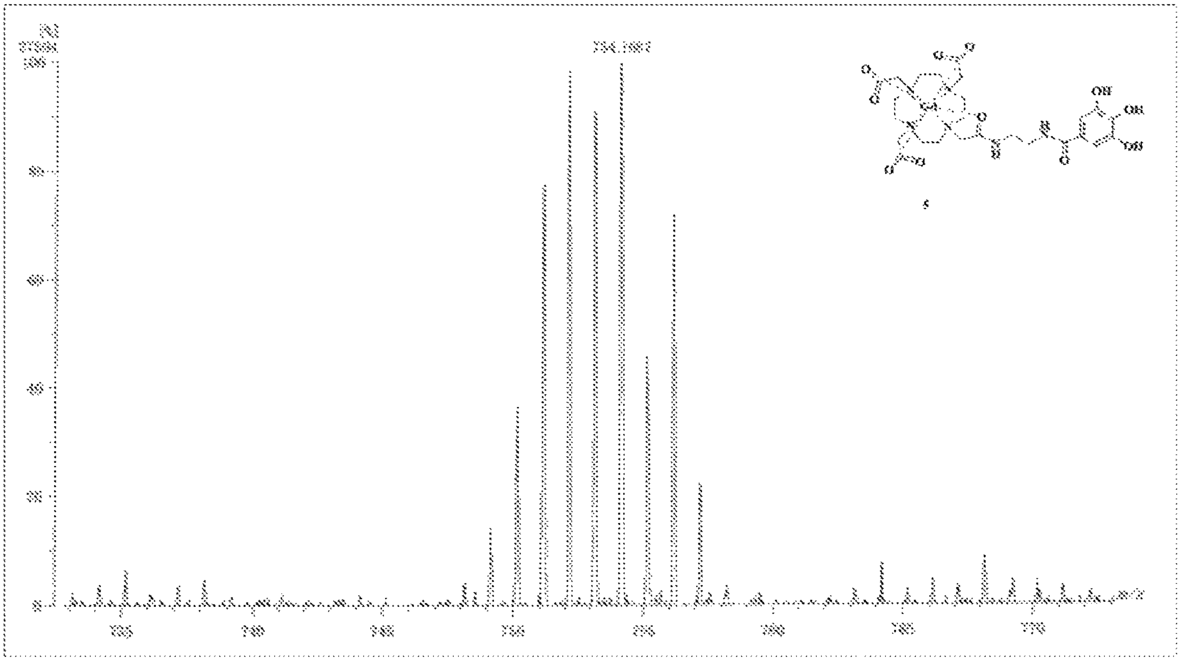
FIG. 4A is a HR-MS spectrum of Gd-DO3A-Ga prepared in Present Example 2 of a compound according to the present disclosure.
Figure 4B:
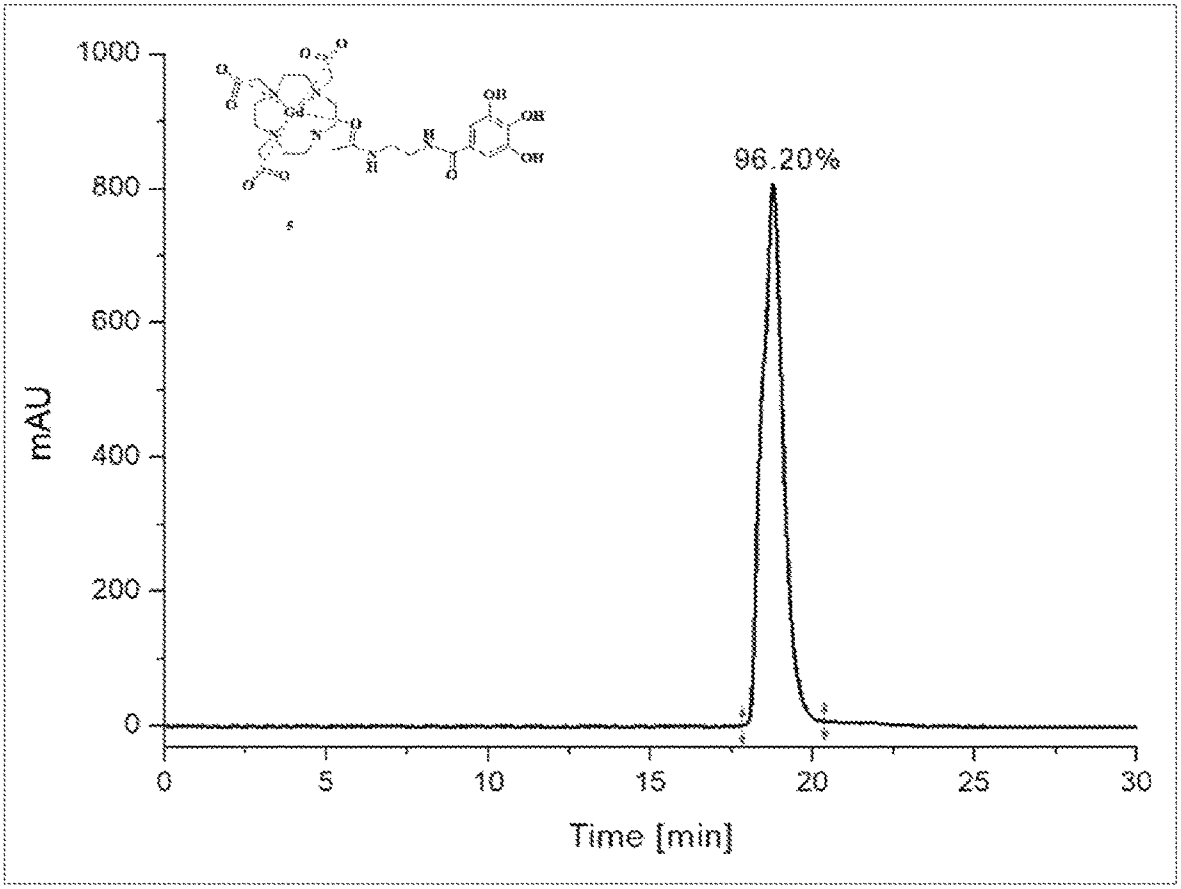
FIG. 4B is an HPLC chromatogram of Gd-DO3A-Ga prepared in Present Example 2 of a compound according to the present disclosure.

HR-MS spectrum and HPLC chromatogram of the obtained Compound Gd-DO3A-Ga are shown in FIG. 4A and FIG. 4B, respectively. (Yield: 0.8 g (63%))

HR-MS (m/z): $[M+H]^+$ calculated for $C_{25}H_{36}N_6O_{11}Gd$, 754.1683; found, 754.1687.

Purity analysis using analytical HPLC: 96%

Hereinafter, characteristic evaluation of the prepared representative compound of the present disclosure was performed to determine whether the prepared representative compound of the present disclosure can be used as an MRI contrast material, and at the same time, has a targeting ability towards the amyloid beta polymer.

2. Methods and Results of Characteristic Evaluation of Compound According to the Present Disclosure 1) Measurement of Relaxivity Relaxivity (r1, r2) of each of Gd-DO3A-Ga synthesized using the method according to Present Example 2, and Gadovist® and Dotarem® as commercial cyclic contrast agents as comparative groups.

Specifically, a phantom was prepared by diluting the gadolinium complex to 5 concentrations (0.0625, 0.125, 0.25, 0.5, 1 mM) using tertiary distilled water, and then $T_1$ and $T_2$ relaxation times thereof were measured in 3 T MRI. Thus, R (relaxivity=1/T) thereof at each of the concentrations was calculated and a result of the relaxivity of the gadolinium complex was obtained via linear regression analysis. (See following Table 1 and FIG. 5)

TABLE 1

| | $r_1$ | $r_2$ |
|---|---|---|
| Gd-DO3A-Ga | 4.04 ± 0.09 | 4.82 ± 0.11 |
| Gadovist ® | 3.85 ± 0.09 | 4.87 ± 0.11 |
| Dotarem ® | 3.40 ± 0.07 | 3.88 ± 0.16 |

Figure 5:
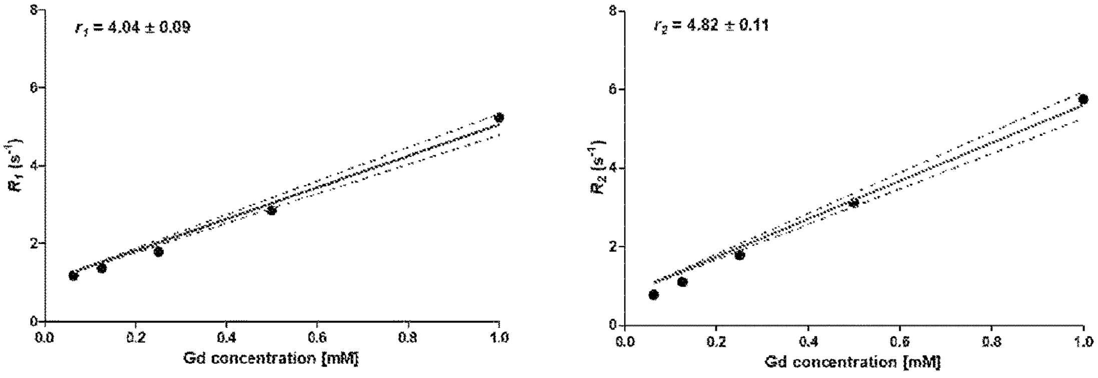
FIG. 5 shows an analysis graph of magnetic relaxivity ($r_1$, $r_2$) of Gd-DO3A-Ga according to the present disclosure.

It was identified as shown in the above Table 1 and FIG. 5 that a $r_1$ value of Gd-DO3A-Ga was measured to be 4.04±0.09 and a r2 value thereof was measured to be 4.82±0.11, which are respectively similar to or slightly larger than those of each of the cyclic commercial contrast agents as the comparison groups. Thus, the contrast medium of the present disclosure exhibited sufficient relaxivity for clinical use.

2) Kinetic Stability Evaluation

Figure 6:
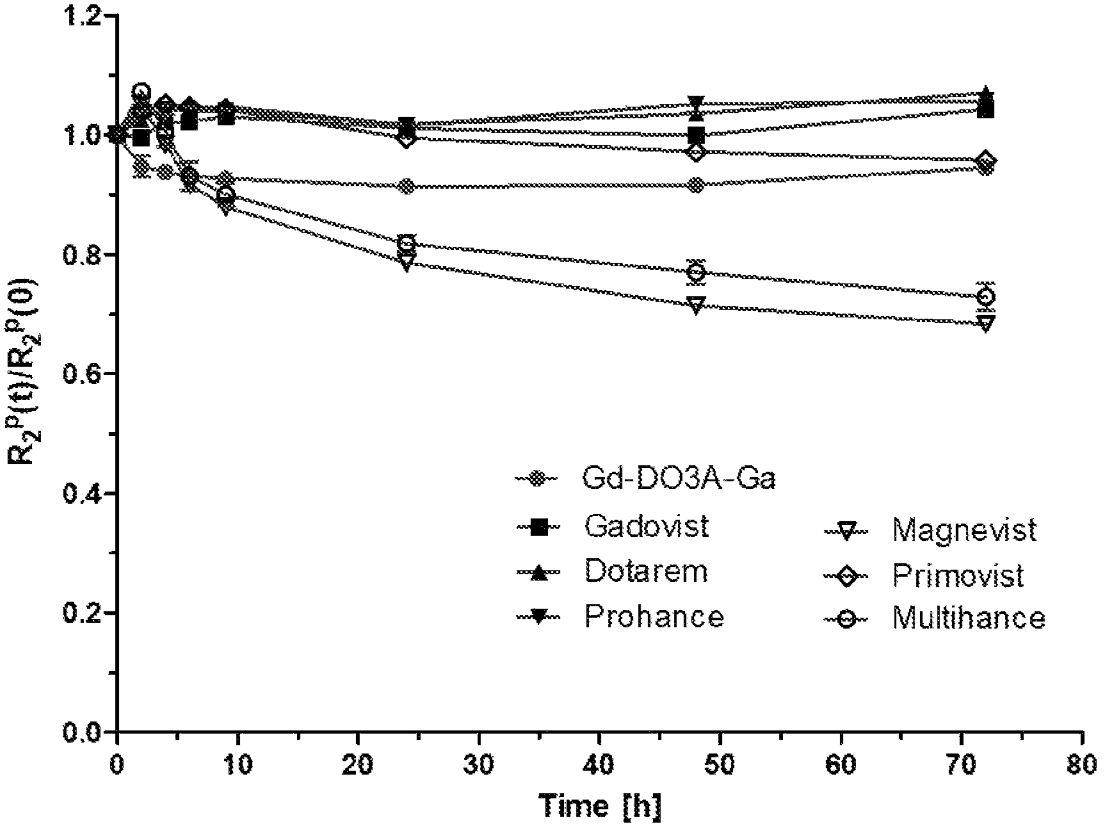
FIG. 6 shows a graph of kinetic stability of each of Gd-DO3A-Ga according to the present disclosure and several commercial contrast agents (Gadovist, Dotarem, Prohance, Magnevist, Primovist, Multihance).

A phantom was prepared by diluting each of Gd-DO3A-Ga and several commercial contrast agents (Gadovist, Dotarem, Prohance, Magnevist, Primovist, Multihance) to a concentration of 2.5 mM using PBS (pH 7.4), and then 250 mM of zinc chloride ($ZnCl_2$) was added, at 1 equivalent, thereto. Binding stability of DO3A ligand and Gd metal ions was evaluated, and a result is shown in FIG. 6. This may be identified by measuring transmetallation of gadolinium ions due to zinc ions as a change in the relaxivity.

As shown in FIG. 6, the synthesized Gd-DO3A-Ga maintains a value of $R_2$ change at a large value of 0.9 or greater and thus has sufficient stability to be used as an MRI contrast agent.

3) Phantom Test Method for Identification Whether Compound has Targeting Ability Toward Amyloid Beta Polymer HFIP (221.5 μl) was added to amyloid beta (1 mg, 1 mM) to produce a mixture which in turn was shaken for 1 hour at room temperature using a shaker to remove preaggregation.

Next, the amyloid beta from which the pre-aggregation was removed was dried. Then, DMSO (221.5 μl) was added thereto to adjust a concentration thereof to 1 mM. Then, a suspension thereof was produced using a mixer and a sonicator, and PBS (1×, pH 7.4, 878.5 μl) was added to the suspension to adjust a concentration of the suspension to 0.2 mM.

Thereafter, the suspension was subjected to incubation for 4 days at 37° C. using a shaker. Then, amyloid beta polymer (oligomeric Aβ) that has been polymerized was dispensed by 200 μl. Then, a further mixed solution in which the compound Gd-DO3A-Ga was dissolved in PBS at a concentration of 2 mM was added thereto at 20 μl amount. A further mixed solution in which the commercial contrast agent (Gadovist®) was dissolved in PBS at a concentration of 2 mM was added thereto at 20 μl amount. Then, each of two resulting mixtures was incubated at 37° C. for 24 hours using a shaker.

After completion of the incubation, a supernatant was removed therefrom via centrifugation, and then the amyloid beta polymer was washed with PBS, and then 200 μl of PBS:DMSO=9:1 solution was added to a pellet thereof to prepare MRI phantom samples.

4) Experimental Results

Figure 7:
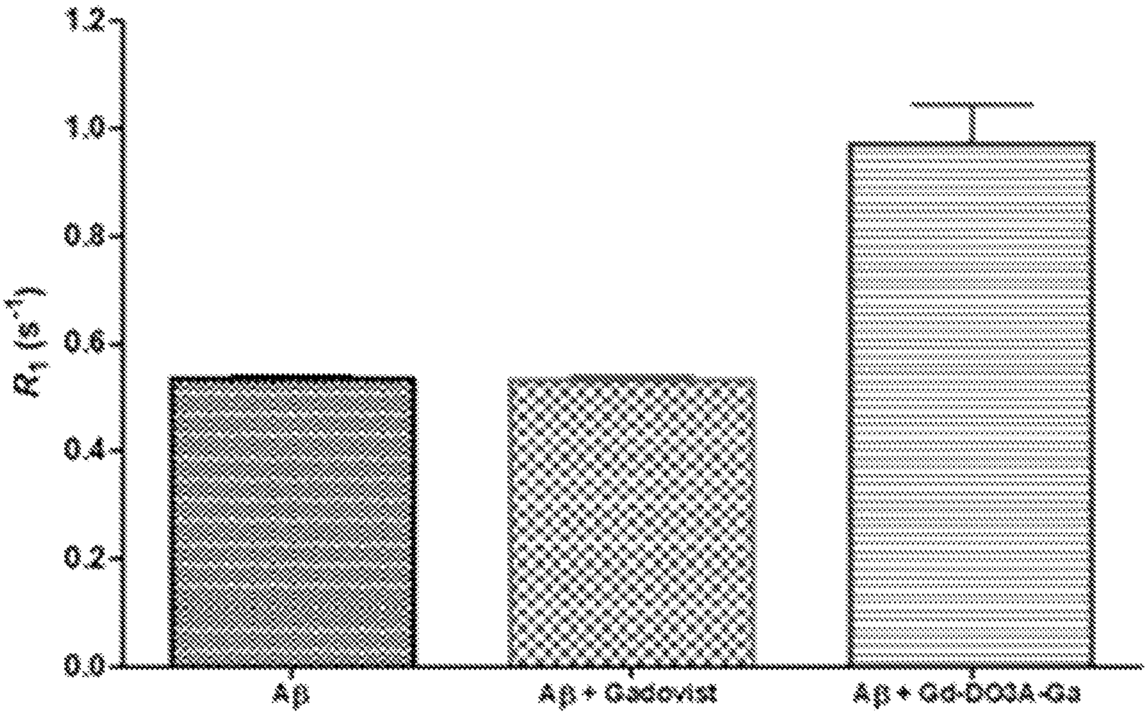
FIG. 7 shows a graph of a comparing result of MR signal intensities of MRI phantom samples.

The amyloid beta polymer targeting ability test experiment was carried out in 9.4 T MR equipment, and a result is shown in FIG. 7. FIG. 7 shows a graph of a comparing result of MR signal intensities of the MRI phantom samples.

Referring to FIG. 7, a contrast enhancement effect of the phantom (control) incubated only with the amyloid beta polymer and a contrast enhancement effect of the phantom (comparative example) incubated with both of the commercial contrast medium (Gadovist®) and the amyloid beta polymer had no significant difference from each other. Thus, it was identified that the commercial contrast agent (Gadovist®) used as the comparative example had no targeting effect toward the amyloid beta polymer.

On the contrary, the phantom incubated with GD-DO3A-Ga as the compound according to the present disclosure and the amyloid beta polymer exhibited a signal intensity that was higher than two times of that of the control. Thus, it may be identified that the compound according to the present disclosure has a targeting effect toward amyloid beta polymer. Thus, it may be identified that Gd-DO3A-Ga of the present disclosure is suitable as an amyloid beta polymer targeting contrast agent.

Although the above disclosure has been described with reference to a preferred embodiment of the present disclosure, those skilled in the art may variously modify the present disclosure within the scope not departing from the spirit and scope of the present disclosure described in the claims below.

What is claimed is:

1. A gadolinium-based compound represented by a following Chemical Formula 1:

(Chemical Formula 1)

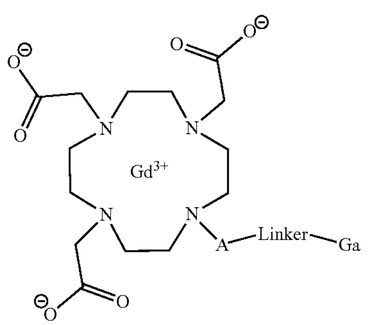

wherein in the Chemical Formula 1,

A represents *—$(CH_2)_n$-$A^1$-*, n represents any integer from 0 to 5, $A^1$ represents *—COO—*, *—CO—*, *—NH—*, *—$CH_2$—*, *—CONH—*, or *—O—*, Linker represents *-$L^1$-NHCO-$L^2$-*, *-$L^1$-O—R—O-$L^2$-*, *-$L^1$-$CH_2$-$L^2$-*, *-$L^1$-NH-$L^2$-*, or *-$L^1$-COO-$L^2$-*, $L^1$ represents linear or branched (C1-C30)alkyl, $L^2$ represents a single bond, hydrogen or linear or branched (C1-C30)alkyl, R represents linear or branched (C1-C20)alkyl, Ga represents a following Chemical Formula 2:

(Chemical Formula 2)

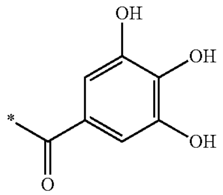

* indicates a connection site.

2. The gadolinium-based compound of claim 1, wherein n represents any integer from 1 to 5, and $A^1$ represents *—CONH—*.

3. The gadolinium-based compound of claim 1, wherein $L^1$ represents linear or branched (C1-C10)alkyl, and $L^2$ represents the single bond.

4. The gadolinium-based compound of claim 1, wherein the gadolinium coordinates with at least one water molecule.

5. The gadolinium-based compound of claim 1, wherein the compound specifically binds to mammalian amyloid beta polymer.

6. An MRI contrast agent comprising the gadolinium-based compound of claim 1.

7. The MRI contrast agent of claim 6, wherein the agent is used for diagnosis of a degenerative brain disease.

8. The MRI contrast agent of claim 7, wherein the agent is used for diagnosis of Alzheimer's disease.

9. A method for preparing the gadolinium-based compound of claim 1, the method comprising following steps:

(a) reacting a compound represented by a following Chemical Formula 1-1 with a halogen compound to obtain a following Chemical Formula 1-2:

(Chemical Formula 1-1)

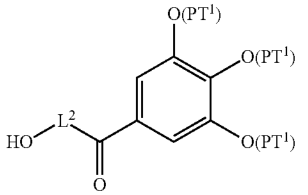

(Chemical Formula 1-2)

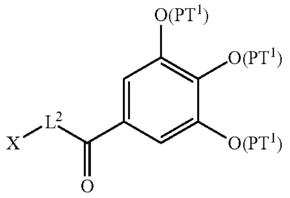

wherein in each of the Chemical Formulas 1-1 and 1-2, $PT^1$ represents a protecting group, X represents a halogen atom, $L^2$ is the same as defined in claim 1;

(b) reacting the compound of the Chemical Formula 1-2 with a compound represented by a following Chemical Formula 1-3 to obtain a compound represented by a following Chemical Formula 1-4:

(Chemical Formula 1-3)

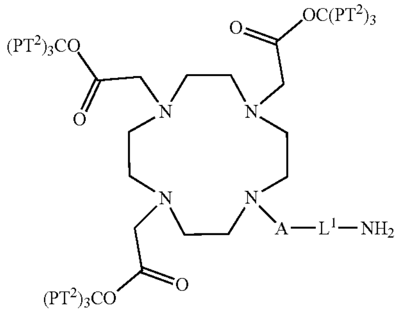

-continued (Chemical Formula 1-4)

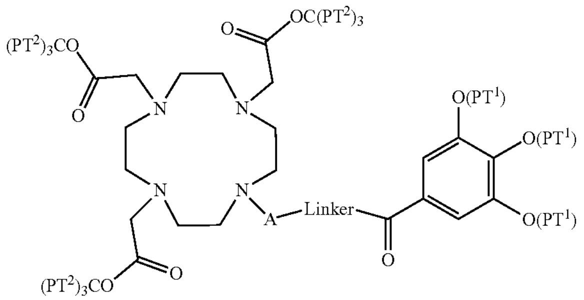

wherein in each of the Chemical Formulas 1-3 and 1-4, each of $PT^1$ and $PT^2$ individually represents a protecting group, Linker represents *-$L^1$-NH-$L^2$-*, each of $L^1$, $L^2$, and A is the same as defined in claim 1;

(c) removing $PT^1$ and $PT^2$ from the compound of the Chemical Formula 1-4; and (d) reacting a compound obtained in the step (c) with gadolinium hydrate to obtain the compound of the Chemical Formula 1.

10. The method of claim 9, wherein in the step (a), $L^2$ represents the single bond, and the halogen compound is thionyl chloride.

11. A method for preparing the gadolinium-based compound of claim 1, the method comprising following steps:

(a) reacting a compound represented by a following Chemical Formula 2-1 with a compound represented by a following Chemical Formula 2-2 to obtain a following Chemical Formula 2-3:

(Chemical Formula 2-1)

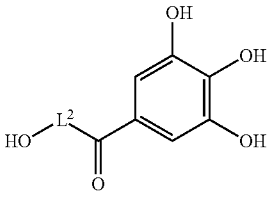

(Chemical Formula 2-2)

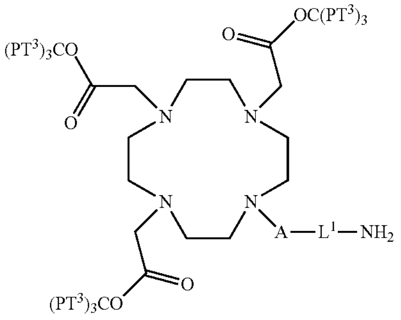

-continued (Chemical Formula 2-3)

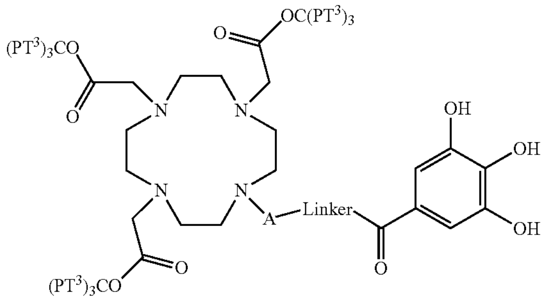

wherein in each of the Chemical Formulas 2-1 to 2-3, $PT^3$ represents a protecting group, Linker represents *-$L^1$-NH-$L^2$-*, each of $L^1$, $L^2$, and A is the same as defined in claim 1;

(b) removing $PT^3$ from the compound of the Chemical Formula 2-3; and (c) reacting a compound obtained in the step (b) with gadolinium hydrate to obtain the compound of the Chemical Formula 1.

12. The method of claim 11, wherein in the step (a), $L^2$ represents the single bond.

* * * * *